(12) United States Patent
Hilliard et al.

(10) Patent No.: US 9,524,856 B2
(45) Date of Patent: Dec. 20, 2016

(54) IN-CHAMBER FLUID HANDLING SYSTEM AND METHODS HANDLING FLUIDS USING THE SAME

(71) Applicant: ELECTRO SCIENTIFIC INDUSTRIES, INC., Portland, OR (US)

(72) Inventors: Shane Hilliard, Bozeman, MT (US); Ciaran J O'Connor, Bozeman, MT (US); Jay Wilkins, Belgrade, MT (US); Erik Larsen, Bozeman, MT (US); Leif Summerfield, Bozeman, MT (US)

(73) Assignee: Electro Scientific Industries, Inc., Portland, OR (US)

( * ) Notice: Subject to any disclaimer, the term of this patent is extended or adjusted under 35 U.S.C. 154(b) by 143 days.

(21) Appl. No.: 14/174,677

(22) Filed: Feb. 6, 2014

(65) Prior Publication Data
US 2014/0223991 A1    Aug. 14, 2014

Related U.S. Application Data

(60) Provisional application No. 61/762,860, filed on Feb. 9, 2013.

(51) Int. Cl.
*H01J 49/04* (2006.01)
*G01N 1/22* (2006.01)
*G01N 1/38* (2006.01)

(52) U.S. Cl.
CPC ......... *H01J 49/0459* (2013.01); *G01N 1/2226* (2013.01); *H01J 49/0463* (2013.01);
(Continued)

(58) Field of Classification Search
CPC .................... G01N 1/2226; G01N 2001/2241; G01N 2001/383; H01J 49/04; H01J 49/0463; H01J 49/0459
See application file for complete search history.

(56) References Cited

U.S. PATENT DOCUMENTS

| 4,220,414 A | 9/1980 | Barringer |
| 5,240,553 A * | 8/1993 | Jones ............... B23K 26/362 216/63 |

(Continued)

FOREIGN PATENT DOCUMENTS

| JP | 11-201945 | 7/1999 |
| WO | WO94/17385 | 8/1994 |

OTHER PUBLICATIONS

Habicht, Steven C., et al. "Laser-induced acoustic desorption coupled with a linear quadrupole ion trap mass spectrometer." Analytical chemistry 82.2 (2009): 608-614.*

(Continued)

*Primary Examiner* — Lisa Caputo
*Assistant Examiner* — Punam Roy

(57) ABSTRACT

A sample chamber is configured to accommodate a target such that a portion of the target is removable as a sample. A carrier gas injection system is configured to introduce a carrier gas into the sample region from a first position and a second position within the sample chamber such that at least a portion of the sample is entrainable by the carrier gas within the sample region. A portion of the sample region is located between the first position and the second position. A sample transport conduit is configured to transport at least a portion of the sample entrained by the carrier gas to a location outside the sample chamber.

29 Claims, 3 Drawing Sheets

(52) U.S. Cl.
CPC ............ *G01N 2001/2241* (2013.01); *G01N 2001/383* (2013.01); *H01J 49/04* (2013.01)

(56) References Cited

U.S. PATENT DOCUMENTS

| | | | |
|---|---|---|---|
| 5,482,524 | A | 1/1996 | Nakano et al. |
| 5,662,762 | A * | 9/1997 | Ranalli ............... B08B 7/0042 156/707 |
| 5,795,396 | A * | 8/1998 | Ishihara ................ C23C 16/24 118/724 |
| 6,062,065 | A | 5/2000 | Sugimoto et al. |
| 6,793,736 | B2 * | 9/2004 | Sandhu ............ H01L 21/67069 134/1 |
| 8,207,494 | B2 * | 6/2012 | Hieftje ............... H01J 49/0004 250/281 |
| 8,319,964 | B2 * | 11/2012 | Hahn ................... G01N 21/718 356/318 |
| 8,742,334 | B2 * | 6/2014 | Molloy ................ H01J 49/105 204/157.41 |
| 2002/0020813 | A1 | 2/2002 | Shiokawa et al. |
| 2004/0020511 | A1 | 2/2004 | Sandhu et al. |
| 2004/0045497 | A1 | 3/2004 | Kriews et al. |
| 2005/0167598 | A1 * | 8/2005 | Bujas ................ G01N 15/0826 250/356.2 |
| 2006/0049034 | A1 * | 3/2006 | Lee ...................... B01J 19/088 204/192.12 |
| 2007/0009385 | A1 | 1/2007 | Watanabe |
| 2009/0272893 | A1 * | 11/2009 | Hieftje ............... H01J 49/0004 250/282 |
| 2010/0207038 | A1 * | 8/2010 | Sharp ................ B23K 26/1405 250/492.1 |
| 2011/0006297 | A1 * | 1/2011 | Inoue ................ H01L 21/02565 257/43 |
| 2011/0240839 | A1 * | 10/2011 | Hutchinson ........ H01J 49/0409 250/282 |
| 2012/0008139 | A1 | 1/2012 | Miziolek et al. |
| 2012/0099103 | A1 * | 4/2012 | Hahn ................... G01N 21/718 356/316 |
| 2012/0104244 | A1 * | 5/2012 | Verbeck, IV .......... G01N 1/42 250/282 |
| 2012/0193349 | A1 * | 8/2012 | Callahan ........... H01L 21/02551 219/600 |
| 2013/0042703 | A1 * | 2/2013 | Hutchinson .......... H01J 49/105 73/864.84 |
| 2013/0162991 | A1 * | 6/2013 | O'Connor ............ G01J 3/0291 356/317 |
| 2013/0168545 | A1 * | 7/2013 | Clem .................. H01J 49/0004 250/282 |
| 2014/0227776 | A1 * | 8/2014 | Sharp ..................... G01N 1/28 435/309.1 |
| 2015/0008313 | A1 * | 1/2015 | Loboda ................. H01J 49/164 250/282 |
| 2016/0049283 | A1 * | 2/2016 | Gunther ............. H01J 49/0463 250/423 R |

OTHER PUBLICATIONS

Cheng, Sy-Chyi, et al. "Using laser-induced acoustic desorption/electrospray ionization mass spectrometry to characterize small organic and large biological compounds in the solid state and in solution under ambient conditions." Analytical chemistry 81.3 (2008): 868-874.*

PCT Search Report from PCT/US2014/015173 dated May 12 1014, 13 pages.

European Search Report Issued Sep. 9, 2016 concerning European Patent Application No. EP14749219, which corresponds with the subject U.S. Appl. No. 14/174,677. 8 pages.

* cited by examiner

IN-CHAMBER FLUID HANDLING SYSTEM AND METHODS HANDLING FLUIDS USING THE SAME

RELATED APPLICATIONS

This application claims benefit of U.S. Provisional Patent Application No. 61/762,860 filed on 9 Feb. 2013.

BACKGROUND

Embodiments of the present invention as exemplarily described herein relate generally to apparatuses for handling fluids within a chamber and to methods of handling fluids within a chamber. More particularly, embodiments of the present invention relate to apparatuses and methods capable of effectively delivering a carrier gas over a target disposed within a chamber and for efficiently purging a chamber of a fluid.

Analysis systems, such as mass spectrometry (MS) systems, optical emission spectrometry (OES) systems and the like, can be used to analyze the composition of a target (e.g., a solid target material). Often, a sample of the target is provided to an analysis system in the form of an aerosol. As is known in the art, an aerosol generally characterized as a colloid suspension of solid and possibly liquid particles in a carrier gas such as helium (He). The aerosol is typically produced by arranging the target in a sample chamber, introducing a flow of a carrier gas within the sample chamber, and ejecting a portion of the target (e.g., by ablating a portion of the target with laser light), in the form of particles. Thereafter, the ejected particles are typically entrained by the flowing carrier gas and transported to an analysis system via a sample transport conduit.

Generally, the sample chamber includes an access opening that permits passage of the target into and out of the sample chamber. However, if the sample chamber is located in an environment containing atmospheric gases (e.g., oxygen, nitrogen, carbon dioxide, etc.) the atmospheric gases can invade the interior of the sample chamber whenever the target passes through the access opening. Atmospheric gases within the sample chamber can mix with the flowing carrier gas and be delivered to the analysis system with the sample. As a result, the quality of the analysis performed by the analysis system can be degraded due to the presence of the atmospheric gases with the sample. The presence of atmospheric gases such as oxygen and nitrogen in the sample chamber can also cause formation of interfering species that are ultimately transported to the analysis system, which can also degrade the quality of the analysis performed by the analysis system. The presence of atmospheric gases within the sample chamber is also problematic because a varied or inhomogenous distribution of gases within the sample chamber can cause a different analytical response to samples generated from different areas of the target, ultimately leading to poor positional reproducibility of the analytical technique. Therefore, a user will get a different analytical result from the same target depending upon where the sample of the target was obtained.

Conventionally, atmospheric gases are removed from the interior of the sample chamber via a sample transport conduit. However, the inlet of the of the sample transport conduit is typically arranged within a middle or upper portion of the sample chamber at a location selected for optimal collection of the aerosol generated from the target—not for purging atmospheric gases, which can be heavier than, or more dense than, the carrier gas. Therefore conventional atmospheric gas removal techniques which involve the use of the aerosol transport conduit are inefficient, resulting in lengthy purge times and often a residual amount of atmospheric gases within the sample chamber.

Another conventional technique involves the use of a vacuum pump to suck out atmospheric gases from the interior of the sample chamber. In cases where the sample chamber is a laser ablation chamber including a transmission window (typically formed of quartz), a high vacuum generated by the vacuum pump may undesirably crack the transmission window. Therefore, the ability to quickly evacuate atmospheric gases from the laser ablation chamber using the vacuum pump can be significantly impaired.

DETAILED DESCRIPTION OF THE ILLUSTRATED EMBODIMENTS

Figure 1:
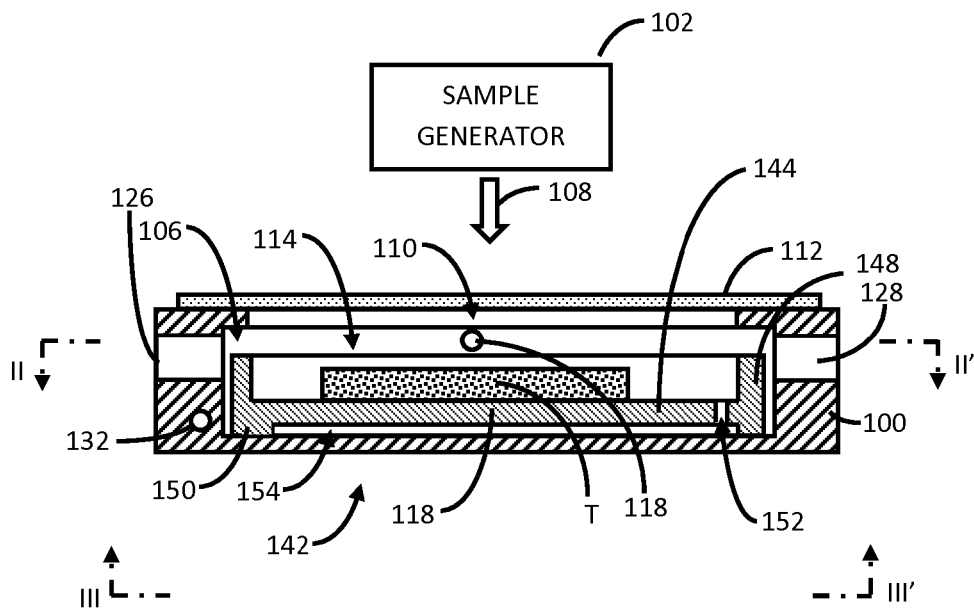
FIG. 1 is a cross-sectional view, taken along line I-I' shown in FIG. 2, schematically illustrating a portion of an apparatus including a sample chamber and a target holder according to one embodiment.

Example embodiments are described below with reference to the accompanying drawings. Many different forms and embodiments are possible without deviating from the spirit and teachings of the invention and so the disclosure should not be construed as limited to the example embodiments set forth herein. Rather, these example embodiments are provided so that this disclosure will be thorough and complete, and will convey the scope of the invention to those skilled in the art. In the drawings, the sizes and relative sizes of components may be exaggerated for clarity. The terminology used herein is for the purpose of describing particular example embodiments only and is not intended to be limiting. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise specified, a range of values, when recited, includes both the upper and lower limits of the range, as well as any sub-ranges therebetween.

Figure 2:
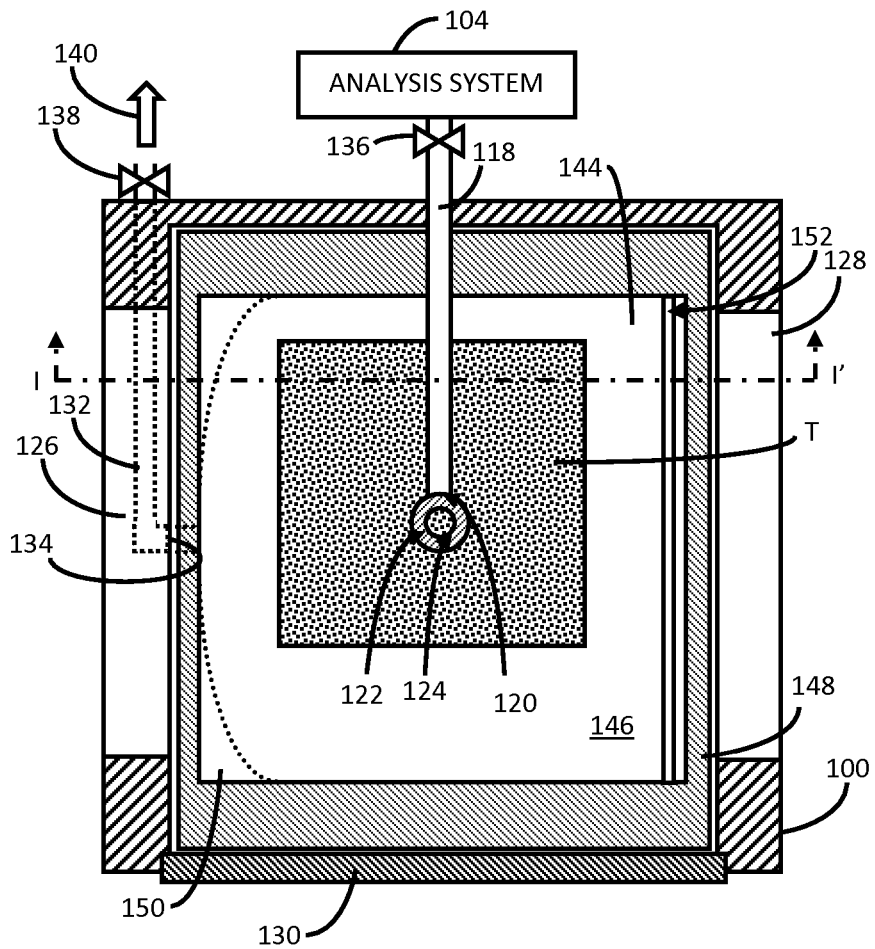
FIG. 2 is a cross-sectional view, taken along line II-II' shown in FIG. 1, schematically illustrating another portion of the apparatus shown in FIG. 1.
Figure 3:
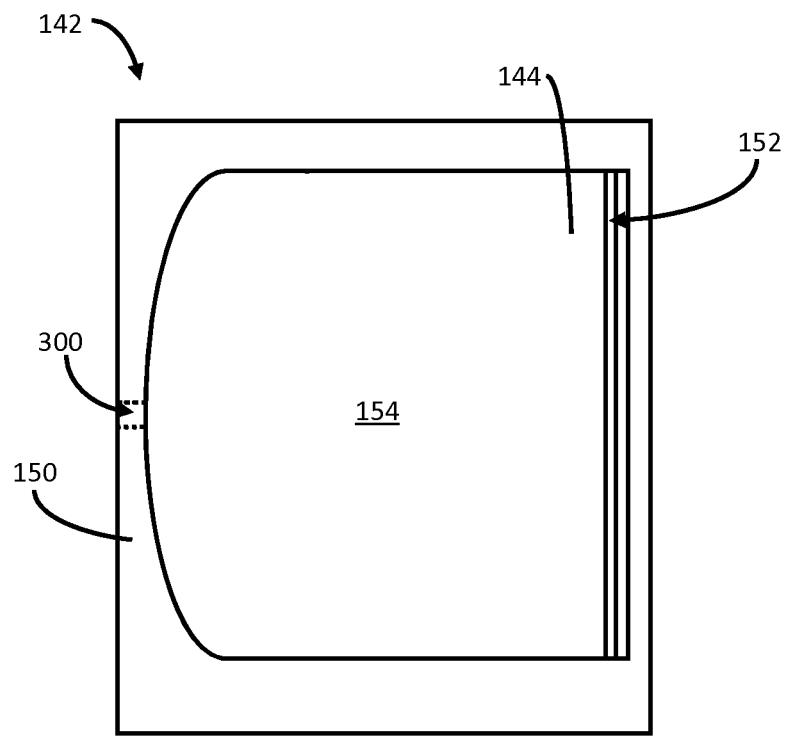
FIG. 3 is bottom plan view, taken along line III-III' shown in FIG. 1, schematically illustrating a lower portion of the target holder shown in FIG. 1.

FIG. 1 is a cross-sectional view, taken along line I-I' shown in FIG. 2, schematically illustrating a portion of an apparatus including a sample chamber and a target holder according to one embodiment. FIG. 2 is a cross-sectional view, taken along line II-II' shown in FIG. 1, schematically illustrating another portion of the apparatus shown in FIG. 1. FIG. 3 is bottom plan view, taken along line III-III' shown in FIG. 1, schematically illustrating a lower portion of the target holder shown in FIG. 1.

Shown in FIGS. 1 and 2 is an apparatus including a sample chamber 100, a sample generator 102, and an analysis system 104. The sample chamber 100 is configured to accommodate a target, such as target T, within an interior 106 thereof. The sample generator 102 is configured to remove a portion of the target T disposed within the interior 106 of the sample chamber 100, thereby generating a "sample" of the target T. The analysis system 104 is configured to analyze a composition of at least a portion of the sample. For example, the analysis system 104 may include a mass spectrometry system, an optical emission spectrometry system, or the like or a combination thereof. In one embodiment, the apparatus may further include a sample preparation system (not shown) configured to excite (e.g., ionize, atomize, illuminate, heat, or the like or a combination thereof) one or more components of at least a portion of the sample before the sample is analyzed by the analysis system 104.

Generally, the sample chamber 100 is configured to facilitate removal of a portion of the target T by the sample generator 102 when the target T is accommodated within the interior 106. For example, in the illustrated embodiment, the sample chamber 100 may be provided as a laser ablation chamber, and the sample generator 102 may include one or more lasers configured to generate a sample of the target T by directing a beam of laser light (e.g., including one or more pulses of laser light) along the direction indicted arrow 108, into the interior 106 of the sample chamber 100 to irradiate a region of the target T accommodated therein. In such an example, the sample chamber 100 may include an optical port 110 permitting optical communication between the sample generator 102 and the interior 106 of the sample chamber 100. Optionally, a transmission window 112 may be provided to prevent material (e.g., particles of the target material) from exiting the interior 106 of the sample chamber 100 through the optical port 10. The transmission window 112 is typically formed of a material (e.g., quartz) that is at least substantially transparent to the laser pulses generated by the sample generator 102. The transmission window 112 may also be sealed to the sample chamber 100 to prevent dust, debris or other unwanted gases or other sources of contamination from entering into the interior 106 through the optical port 110. One or more characteristics such as wavelength (e.g., in a range from about 157 nm to about 11 µm, such as 193 nm, 213 nm, 266 nm, or the like), pulse duration (e.g., in a range from about 100 femtoseconds to about 25 nanoseconds), spot size, pulse energy, average power, peak power, temporal profile, etc., of each laser pulse can be selected or otherwise controlled to ablate material of target T that is located within or adjacent to the irradiated region. The sample generator 102 may also include laser optics (e.g., one or more lenses, beam expanders, collimators, apertures, mirrors, etc.) configured to modify laser light generated by one or more of the lasers.

As used herein, the removal of material by laser ablation can involve one or more mechanisms such as opto-electronic absorption of laser energy at the surface of the target T, energy transfer from initially-excited electrons to acoustic phonons, thermal heating of the surface of the target T, plasma initiation above the surface of the target T, cooling and conglomeration of particles and particle clusters, phase explosion causing ejection of particulates, exfoliation of material flakes, generation of chips, and the like. Upon being ablated, material of target T that is located within or adjacent to the irradiated region (also referred to herein as "target material") is ejected, displaced or otherwise transported from the target T as a sample, typically in the form of a plume containing particles, etc., of the target material. The region of the interior 106 into which the sample can be ejected, displaced or otherwise transported is referred to herein as a sample region 114. Thus, the sample region 114 may extend along a first direction (e.g., along a vertical direction, as illustrated) within the interior 106, from the target T towards the optical port 110, and may also extend along a second direction (e.g., along a lateral direction, as illustrated) toward sides of the sample chamber 100.

In one embodiment, the target T may be positionally fixed relative to the beam of laser light output by the sample generator 102 when the target T is accommodated within the interior 106. In another embodiment, however, the target T may be moved relative to the beam of laser light output by the sample generator 102 when the target T is accommodated within the interior 106. For example, one or both of the sample generator 102 and the beam 108 may be moved or scanned relative to the transmission window 110. In another example, the target T may be moved within the interior 106 relative to one or both of the sample chamber 100 and the sample generator 102. In yet another example, the sample chamber 100 may be moved relative to the sample generator 102. Thus it will be appreciated that the lateral extent of the sample region 114 may also correspond to the degree of relative movement achievable between one or more of the target T, the sample chamber 100, the sample generator 102, and the beam of laser light output by the sample generator 102.

To facilitate analysis of at least a portion of the removed portion of the target T by the analysis system 104, the apparatus may include a sample transport conduit 118 configured to transport at least a portion of the sample from a location within the interior 106 to a location outside the sample chamber 100. As best shown in FIG. 2, the sample transport conduit 118 may be provided as a pipe or tube extending through the sample chamber 100 so as to be in fluid communication with the interior 106 of the sample chamber 100. The sample transport conduit 118 generally includes an inlet 120 located at one end thereof and configured to receive or otherwise collect at least a portion of the sample ejected from the target T, and an outlet located at another end thereof, which is fluidly coupled to the analysis system 104 (or to the sample preparation system). Constructed as described above, the sample transport conduit 118 is configured to transport at least a portion of the sample received at the inlet 120 through the outlet thereof.

In the embodiment exemplarily illustrated in FIG. 2, the sample transport conduit 118 is inserted through a sample port extending through the sample chamber 100 to extend beyond the sample chamber 100 and into the interior 106 such that the inlet 120 is disposed within the sample region 114. In other embodiments, however, the sample transport conduit 118 is inserted partially or only completely through the sample port such that the inlet 120 is disposed within the sample chamber 100 and is either flush with, or recessed relative to, an adjacent surface of the sample chamber 100 exposed to the interior 106. The inlet 120 may be positionally fixed relative to the body of the sample transport conduit 118 (i.e., the sample transport conduit 118 may be a substantially rigid structure), or may be positionally variable relative to the body of the sample transport conduit 118 (i.e., the sample transport conduit 118 is a flexible structure). The position of the inlet 120 relative to the interior 106 may be fixed or may be variable. Further, the position of the inlet 120 relative to the sample generator 102 or a beam of laser light output by the sample generator 102 may be fixed or may be variable.

In the embodiment exemplarily illustrated in FIG. 2, a sample cell 122 may be coupled to the inlet 120 and extend along the aforementioned first direction from the inlet 120 to be closely adjacent to the target T. The sample cell 122 may have a generally annular shape defining a central sample collection region 124 open at a first end at a location relatively close to the target T and at a second end at a location relatively distant from the target T. The sample cell 122 may be structured such that the beam of laser light transmitted into the interior 106 through the transmission window 112 and optical port 110 is also transmittable through the first and second ends of the central sample collection region 124 before impinging upon the target T. At least a portion of the sample ejected from the target T is transferred into the central sample collection region 124 through the first end thereof. Once transferred into the central sample collection region 124, the sample can be collected into the inlet 120 and thereafter transported to the analysis system 104 either directly from the sample transport conduit 118 or via the sample preparation system.

To facilitate collection of the sample into the inlet 120, the apparatus may further include a carrier gas injection system configured to introduce carrier gas into the sample region 114 such that such that at least a portion of the sample is entrainable by the carrier gas within the sample region 114. Generally, the carrier gas is selected to be at least substantially inert with respect to the sample generated within the interior 106. Helium is an example of such a suitable carrier gas. It will be appreciated that the carrier gas, along with the portion of the sample entrained with the carrier gas, may be received at the inlet 120 (either directly, or indirectly via the sample collection cup 122).

Generally, carrier gas injection system may include injection nozzles configured to introduce separate streams or flows of carrier gas into the sample region 114 from different positions within the interior 106, and along different directions into the sample region 114. For example, the carrier gas injection system may include injection nozzles, such as first injection nozzle 126 and second injection nozzle 128, each configured introduce a separate flow of a carrier gas into the sample region 114. The first injection nozzle 126 may be configured to introduce a first flow of carrier gas, travelling substantially in a first direction from a first position within the interior 106 of the sample chamber 100, into the sample region 114. The second injection nozzle 128 may be configured to introduce a second flow of carrier gas, travelling substantially in a second direction from a second position within the interior 106 of the sample chamber 100, into the sample region 114. As exemplarily illustrated, at least a portion of the sample region 114 is located (e.g., laterally) between the first position and the second position. As exemplarily illustrated, the first and second directions are different from one another.

Although the carrier gas injection system is illustrated as including only two injection nozzles 126 and 128, it will be appreciated that the carrier gas injection system may include a single injection nozzle (e.g., injection nozzle 126 or 128) or more than two injection nozzles. In other embodiments, different injection nozzles of the carrier gas injection system may be configured to introduce separate flows of carrier gas into the sample region 114 along the same direction into the sample region 114 from different positions within the interior 106. One or more characteristics of a flow of carrier gas (e.g., including flow rate, volume, cross-sectional shape or size, pressure, carrier gas composition, etc.) introduced into the sample region 114 by one injection nozzle may be same as or different from one or more corresponding characteristics of a flow of carrier gas introduced into the sample region 114 by another injection nozzle.

Generally, each injection nozzle of the carrier gas injection system is configured to introduce a uniform flow (or at least substantially uniform flow) of carrier gas into the sample region 114 and across a portion of the surface (or across the entire surface) of the target T. The carrier gas is introduced by an injection nozzle such that the flow of the carrier gas across the surface of the target T is laminar or at least quasi-laminar. In the illustrated embodiment, the aforementioned first and second directions both extend substantially along a common axis (e.g., such that the first and second directions substantially oppose one another). In other embodiments, however, the first and second directions may extend along axes that are oblique or perpendicular with respect to one another. Upon providing a substantially uniform flow of carrier gas, which travels in any particular direction along an axis, the flow can be characterized as having a width, measurable along a direction that is transverse to the axis. Generally, the width of any particular flow of carrier gas can be in a range from 10 mm to 1 m. It will be appreciated, however, that the width of any particular flow of carrier gas can be less than 10 mm or greater than 1 m. Moreover, the width of a flow introduced by one injection nozzle may be greater than or equal to the width of a flow introduced by another injection nozzle. Although flows of carrier gas have been described above as being substantially uniform, it will be appreciated that one or more or all of the injection nozzles of the carrier gas injection system can be configured to introduce a flow of carrier gas into the sample region 114 that is divergent or convergent.

As exemplarily illustrated, the sample chamber 100 is provided with an access opening, such as access opening that can be opened and closed (e.g., by an access door or hatch 130). The access opening is structured to permit passage of the target T into and out of the interior 106 of the sample chamber 100. For example, to arrange the target T within the interior 106 of the sample chamber 100, the access opening may be opened by opening the access door 130 or otherwise removing the access door 130 from the sample chamber 100. Upon opening the access opening, the target T may be inserted through the access opening into the interior 106, and atmospheric gases (e.g., oxygen, nitrogen, carbon dioxide, etc.) or other gases (e.g., organic or inorganic pollutants, solvent vapors, etc.), collectively referred to as a "fluid", may invade or otherwise be introduced into the interior 106 of the sample chamber 100 (e.g., including the regions of the interior 106 within the sample region 114 and outside the sample region 114). Generally, the fluid is heavier than, or more dense than, the carrier gas. Thereafter, the access opening may be closed by closing the opening door 130 or otherwise coupling the access door 130 to the sample chamber 100 so as to fluidly isolate the interior 106 of the sample chamber 100 from the environment outside the sample chamber 100.

In embodiments where it would be desirable to facilitate removal of the above-described fluid from the interior 106 before generating a sample of the target T, the apparatus may include a purge conduit, such as purge conduit 132, configured to transport at least a portion of the fluid from the interior 106 to a location outside the sample chamber 100. As best shown in FIG. 2, the purge conduit 132 may be provided as a pipe or tube, inserted into a purge port extending through the sample chamber 100 so as to be in fluid communication with the interior 106 of the sample chamber 100. The purge conduit 132 generally includes an inlet 134 located at one end thereof and configured to receive or otherwise collect at least a portion of the fluid introduced into the interior of the chamber 106, and an outlet located at another end of the purge conduit 132. In one embodiment, the inlet 134 is disposed at a lowermost region of the interior 106 of the sample chamber 100. In the embodiment illustrated in FIGS. 1 and 2, the apparatus includes only a single purge conduit 132 having a single inlet 134. It will be appreciated, however, that the apparatus may include any number of purge conduits 132, each having any number of inlets 134.

To remove at least a portion of the fluid introduced into the interior 106, a purge process may be implemented in which a purge gas is introduced into the interior 106 in a state in which the interior 106 is fluidly isolated from the environment outside the sample chamber 100. Generally, the purge gas may be lighter than, or less dense than, the fluid. In one embodiment, the purge gas may be the same as the carrier gas (e.g., helium). In another embodiment, the purge gas is introduced into the interior 106 via the carrier gas injection system, but may be different from the carrier gas. In one embodiment, a valve coupling the sample transport conduit 118 to the analysis system 104 (or to the sample preparation system), such as valve 136, may be closed to fluidly disconnect the interior of the sample transport conduit 118 and a valve coupled to the purge conduit 132 outside the sample chamber 100, such as valve 138 may be opened to fluidly connect the inlet 134 of the purge conduit 132 to a region or environment outside the sample chamber 100. As purge gas is introduced into the interior 106, the fluid present within the interior 106 is displaced downwardly to the lower portion into the purge region of the interior 106, where it is efficiently collected into the inlet 134 of the purge conduit 132 and transported within the purge conduit 132 to a location outside the sample chamber 100 (e.g., as indicated by arrow 140). After the fluid is beneficially or completely removed from the interior 106, the sample generator 102 may be operated to generate a sample of the target T in the manner described above.

Removal of fluid from the interior 106 in the manner described above ensures at least substantially the same (or beneficially similar) conditions for sample generation, sample excitation, sample analysis, etc., independent of sampling position on the target T within the interior 106. This, therefore, leads to improved positional reproducibility and, in turn, ensures more accurate, more precise analytical data is generated by the analysis system 104. Removal of fluid from the interior 106 in the manner described above also ensures that the amount of the undesirably introduced fluid within the interior 106 can be brought down to acceptable levels (or removed entirely) relatively quickly, which can lead to higher sample throughput and cost savings via reduced usage of purge or carrier gas.

In one embodiment, and as best illustrated in FIG. 1, the apparatus may include a target holder, such as target holder 142, configured to be disposed within the interior 106 of the sample chamber 100 and support the target T within the interior 106. The target holder 142 may be moveable within the interior 106 relative to the inlet 120 of the sample transport conduit 118, may be moveable within the interior 106 relative to the sample chamber 100, or the like or a combination thereof. In one embodiment, the aforementioned access opening may be structured to permit passage of the target holder 142 (with or without the target T supported thereon) into and out of the interior 106 of the sample chamber 100.

Referring now to FIGS. 1 to 3, the target holder 142 include a base 144 having a support surface 146 configured to physically contact the target T. The target holder 142 may further include a target fence 148 extending upwardly from the support surface 146. Thus the support surface 146 and target fence 148 may define a basin having a depth (e.g., corresponding to the height to which the target fence 148 extends above the support surface 146) within which the target T is supportable. During the aforementioned purge process, fluid within the interior 106 at a region above the support surface 146 may collect within the basin of the target holder 142 and be undesirably prevented from being transferred into the inlet 134 of the purge conduit 132. To enable fluid within the basin to be collected into the inlet 134 of the purge conduit 132, one or more fluid transport conduits may be provided to extend through the base 144, the target fence 148, or the like or a combination thereof. Generally, such fluid transport conduits may include a first end in fluid communication with the basin and a second end in fluid communication with a region of the interior 106 outside the basin. The target holder 142 may include any number of fluid transport conduits, provided in any shape or combination of shapes, and arranged within the target holder 142 in any manner (e.g., in an regular pattern or array, randomly, in locations corresponding to the location of one or more injection nozzles). Constructed as described above, a fluid transport conduit can allow fluid, which would otherwise be trapped within the basin during the purge process, to be displaced out of the basin and into the purge region of the interior 106. In one embodiment, the second end of a fluid transport conduit may be elevationally lower than the first end thereof.

In the exemplarily illustrated embodiment, the target holder 142 can further include a foundation 150 extending downwardly from the base 144 to contact a lower surface of the sample chamber 100 defining the interior 106, and a slit-shaped fluid transport conduit 152 extending through the base 144. The base 144, the foundation 150 and the lower surface of the sample chamber 100 defining the interior 106 can be conceptually considered as defining a purge reservoir 154 that is in fluid communication with the fluid transport conduit 152. As illustrated, the fluid transport conduit 152 includes a first end in fluid communication with the basin (e.g., adjacent to the support surface 146) and a second end in fluid communication with the purge reservoir 154. A reservoir outlet 300 (see FIG. 3) extends through the foundation 150 and is configured to transmit fluid from the purge reservoir 154 into the purge region of the interior 106. For example, the reservoir outlet 300 may include a first end configured to receive fluid from the purge reservoir 154 and a second end located proximate to the inlet 134 of the purge conduit 132 at the purge region. Constructed as described above, the fluid transport conduit 152 can allow fluid, which would otherwise be trapped within the basin during the purge process, to be displaced out of the basin and into the purge reservoir 154, and fluid in the purge reservoir 154 can thereafter be transferred to the inlet 134 of the purge conduit 132 via the reservoir outlet 300.

In the embodiment illustrated in FIGS. 1 and 2, a gap exists between the target holder 142 and the surface of the sample chamber 100 defining the interior 106, through which fluid can flow into the purge region to be collected into the inlet 134 of the purge conduit 132. It will be appreciated, however, that the target holder 142 and the sample chamber 100 can be configured such that no gap exists therebetween through which fluid can flow into the purge region.

It will be appreciated that any of the aforementioned injection nozzles may be configured in any suitable or beneficial manner to generate the flows of carrier gas as described above. In one embodiment, an injection nozzle of the carrier gas injection system may include an inlet configured to receive an input stream of the carrier gas and an outlet configured to eject the carrier gas into the interior 106 of the sample chamber 100. The outlet may include a cover having a slit formed therein to shape the flow of ejected carrier gas. In other embodiments, the cover may have a line of closely-spaced holes, an array of micro-holes, etc. to shape the flow of ejected carrier gas. In another embodiment, the outlet may include a laminar insert configured to shape the flow of the ejected carrier gas. In one embodiment, the injection nozzle may include a stream modification section configured to modify at least one characteristic (e.g., flow rate, direction of flow, cross-sectional shape, pressure, etc.) of the input stream to thereby form a modified stream of the carrier gas. In such an embodiment, the outlet may be configured to eject the carrier gas having the modified characteristic(s) into the interior 106 of the sample chamber 100.

Figure 4:
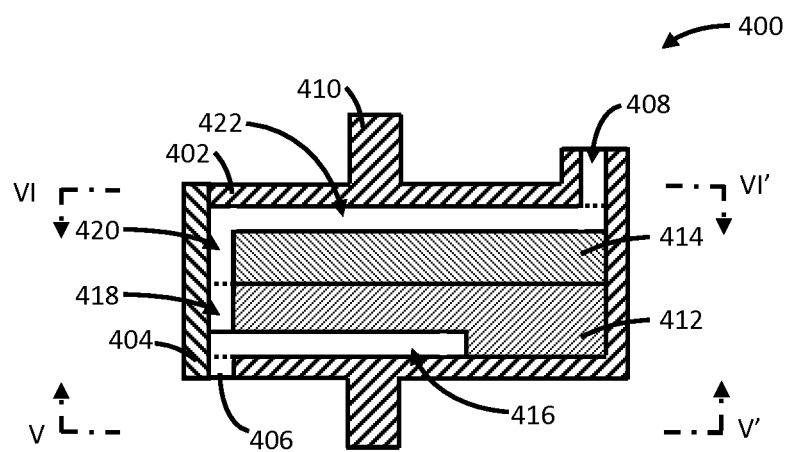
FIG. 4 is a cross-sectional view schematically illustrating a portion of an injection nozzle according to one embodiment.
Figure 5:
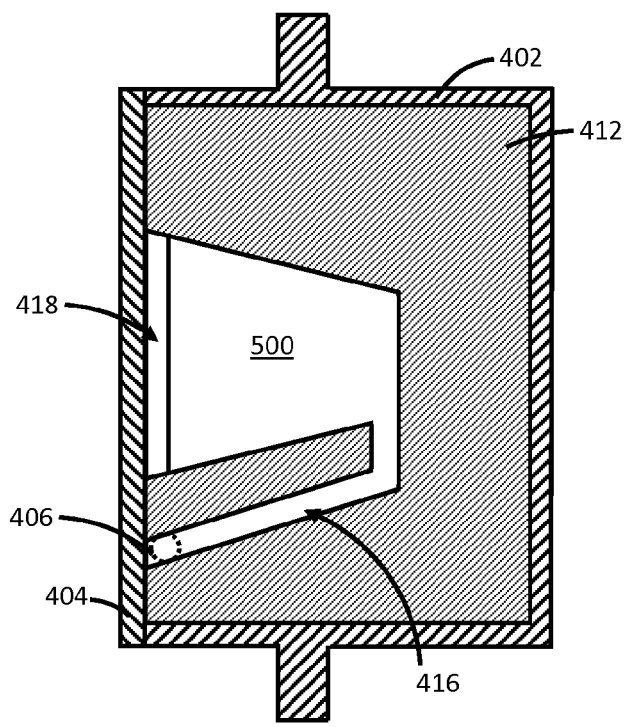
FIG. 5 is bottom plan view, taken along line V-V' shown in FIG. 4, schematically illustrating a lower portion of a first fluid guide shown in FIG. 4.
Figure 6:
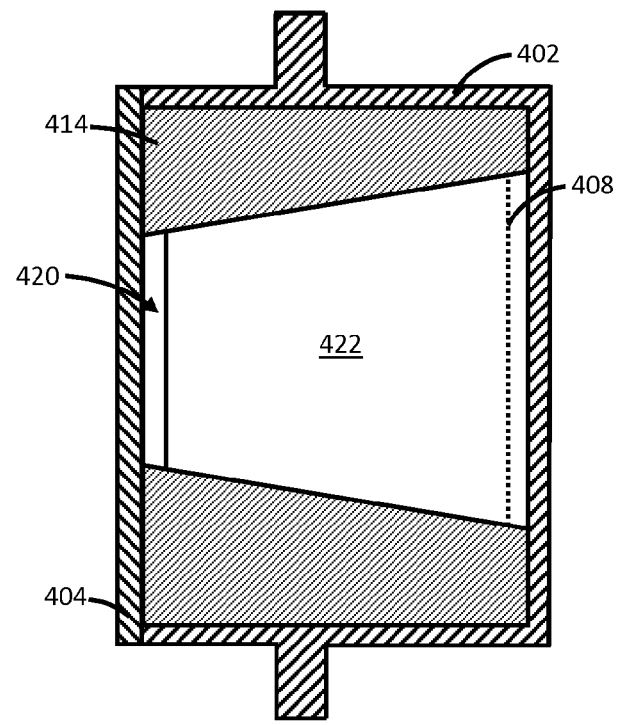
FIG. 6 is bottom plan view, taken along line VI-VI' shown in FIG. 4, schematically illustrating an upper portion of a second fluid guide shown in FIG. 4.

FIG. 4 is a cross-sectional view schematically illustrating a portion of an injection nozzle according to one embodiment. FIG. 5 is bottom plan view, taken along line V-V' shown in FIG. 4, schematically illustrating a lower portion of a first fluid guide shown in FIG. 4. FIG. 6 is bottom plan view, taken along line VI-VI' shown in FIG. 4, schematically illustrating an upper portion of a second fluid guide shown in FIG. 4.

In one embodiment, any of the injection nozzles of the carrier gas injection system may be configured as exemplarily shown in FIG. 4. Referring to FIG. 4, an injection nozzle, such as injection nozzle 400, may include a first body portion 402 and a second body portion 404 adapted to be coupled to each other. An inlet configured to receive a stream of a gas (e.g., a carrier gas) may be formed in the first body portion 402, and an outlet configured to eject a flow of gas into the interior 106 may also be formed in the first body portion 402. A mounting flange 410 may be provided on the first body portion 402, which can be used to couple the injection nozzle 400 to the sample chamber 100. The first body portion 402 can define a cavity configured to receive a first fluid guide 410 and a second fluid guide 412, each of which may be provided as blocks of material (e.g., polymeric material, metallic material, etc.) having channels or grooves formed therein to direct, shape or otherwise modify a flow of gas.

Referring to FIGS. 4 and 5, the first fluid guide 412 can include a first guide channel 416 defined therein configured to transport a gas from the inlet 406 to a first expansion channel 500, which is configured to spread the flow of gas toward a second guide channel 418. Referring to FIGS. 4 and 6, the second fluid guide 414 can include a third guide channel 420 defined therein configured to transport a gas from the second guide channel 416 to a second expansion channel 422, which is configured to spread the flow of gas toward the outlet 408. When the first and second fluid guides 412 and 414 are disposed within the cavity defined by the first body portion, an end of the first guide channel 416 is aligned to the inlet 406, the second guide channel 418 is aligned to the third guide channel 420, and the end of the second expansion channel 422 is aligned with the outlet 408.

The foregoing is illustrative of example embodiments of the invention and is not to be construed as limiting thereof. Although a few example embodiments have been described, those skilled in the art will readily appreciate that many modifications are possible without materially departing from the novel teachings and advantages of the invention. Accordingly, all such modifications are intended to be included within the scope of the invention as defined in the following claims.

What is claimed is:

1. An apparatus, comprising:
   a chamber having an interior and an optical port through which light is transmittable into the interior thereof, wherein the interior is defined, at least in part, by a lower surface of the chamber;
   a target holder disposed within an interior of the chamber, the target holder having a base defining a support surface on which a target is supportable above the lower surface of the chamber and at least one fluid transport conduit extending through the target holder, wherein the at least one fluid transport conduit has a first end in fluid communication with the interior of the chamber and a second end in fluid communication with the interior of the chamber, wherein the second end is further away from the support surface than the first end;
   a carrier gas injection system configured to introduce a carrier gas into the interior of the chamber; and
   a purge conduit in fluid communication with the interior of the chamber at a position elevationally below the support surface, the purge conduit configured to transport the fluid from the interior of the chamber to a location outside the chamber.

2. The apparatus of claim 1, wherein
   the carrier gas injection system configured to introduce a first flow of a carrier gas travelling substantially in a first direction into the interior of the chamber and a second flow of a carrier gas travelling substantially in a second direction into the interior of the chamber, wherein the first direction is different from the second direction.

3. The apparatus of claim 2, wherein the carrier gas injection system is configured such that the first direction extends along an axis that is at least substantially parallel to an axis along which the second direction extends.

4. The apparatus of claim 1, wherein the carrier gas injection system includes at least one injection nozzle.

5. The apparatus of claim 4, wherein the at least one injection nozzle includes:
   an inlet configured to receive an input stream of the carrier gas;
   a stream modification section configured to modify at least one characteristic of the input stream, thereby forming a modified stream of the carrier gas; and
   an outlet configured to eject the modified stream of the carrier gas into the interior of the sample chamber,
   wherein the modified stream has at least one characteristic that is different from that of the input stream.

6. The apparatus of claim 5, wherein the at least one characteristic is selected from the group consisting of flow rate, direction of flow, cross-sectional shape and pressure.

7. The apparatus of claim 1, wherein the chamber includes an access opening configured to permit at least one selected from the group consisting of: passage of the target into the interior of the chamber, and passage of the target out from the interior of the chamber.

8. The apparatus of claim 1, wherein the carrier gas injection system is configured to introduce a carrier gas into the interior of the chamber from a first position and a second position within the chamber.

9. The apparatus of claim 8, wherein a portion of the target holder is located between the first position and the second position.

10. The apparatus of claim 1, further comprising a laser system configured to direct a laser pulse through the optical port and into the interior of the chamber.

11. The apparatus of claim 1, further comprising a sample transport conduit having a first end and a second end opposite the first end, wherein the first end is arranged within the interior of the chamber at a location elevationally between the optical port and the support surface of the target holder, and wherein the second end is arranged outside the chamber.

12. The apparatus of claim 1, wherein the first end of at least one fluid transport conduit is formed in the support surface.

13. The apparatus of claim 1, further including a foundation interposed between the base and the lower surface of the chamber such that a lower surface of the base opposite the support surface is spaced apart from the lower surface of the chamber.

14. The apparatus of claim 13, wherein the second end of at least one fluid transport conduit is formed in the lower surface of the base.

15. The apparatus of claim 1, further including a fence disposed at a peripheral region of the support surface, the fence the extending from the support surface towards the optical port.

16. The apparatus of claim 15, wherein the first end of at least one fluid transport conduit is formed in the fence.

17. The apparatus of claim 1, wherein an inlet of the purge conduit is formed in a side surface of the chamber, wherein the side surface at least partly defines the interior of the chamber and wherein the target holder is spaced apart from the side surface.

18. An apparatus, comprising:
a sample chamber configured to accommodate a target, the sample chamber including a sample region within the interior thereof;
a laser system configured to direct a laser pulse into the sample region to irradiate the target, the laser pulse configured to ablate a material from which the target is formed;
a carrier gas injection system configured to introduce a carrier gas into the sample region from a first position and a second position within the sample chamber such that at least a portion of the ablated material is entrainable by the carrier gas within the sample region, wherein a portion of the sample region is located between the first position and the second position; and
a sample transport conduit configured to transport at least a portion of the ablated material entrained by the carrier gas to a location outside the sample chamber,
wherein the carrier gas injection system configured to introduce a first flow of a carrier gas travelling substantially in a first direction into the sample region and a second flow of a carrier gas travelling substantially in a second direction into the sample region such that at least a portion of the ablated material is entrainable by the carrier gas within the sample region, wherein the first direction is different from the second direction, and
wherein the carrier gas injection system is configured such that the first flow has a width, measured along a direction transverse the to the axis along which the first flow extends, that is greater than 10 mm.

19. An apparatus, comprising:
a sample chamber;
a target holder configured to be disposed within an interior of the sample chamber to define a sample region and a purge region within the interior of the sample chamber, the purge region being outside the sample region, wherein the target holder is further configured to support a target such that at least a portion of the target is disposable within the sample region, wherein the target holder comprises:
a base having a support surface configured to physically contact the target; and
at least one fluid transport conduit extending through the base and having a first end adjacent to the support surface and a second end in fluid communication with the purge region; and
a purge conduit in fluid communication with the interior of the sample chamber, the purge conduit configured to transport a fluid from the purge region to a location outside the sample chamber.

20. The apparatus of claim 19, further comprising:
a carrier gas injection system configured to introduce a carrier gas into the sample region; and
a sample transport conduit in fluid communication with the interior of the chamber at a position above the purge conduit, the sample transport conduit configured to transport at least a portion of the carrier gas from the sample region to a location outside the sample chamber.

21. The apparatus of claim 20, wherein the target holder is moveable relative to an inlet of the sample transport conduit.

22. The apparatus of claim 20, wherein a density of the fluid is greater than a density of the carrier gas.

23. The apparatus of claim 20, wherein the carrier gas includes helium.

24. The apparatus of claim 19, wherein the target holder is moveable relative to the sample chamber.

25. The apparatus of claim 19, wherein the target holder is configured so that, when the target holder is disposed within the interior of the sample chamber, a purge reservoir is defined below the sample region, and comprises the purge region.

26. The apparatus of claim 25, wherein the target holder includes a reservoir outlet configured to transmit fluid in the purge reservoir to a location within the interior of the sample chamber that is outside the purge reservoir.

27. The apparatus of claim 19, wherein the purge region is located below the sample region.

28. The apparatus of claim 19, wherein the fluid includes at least one selected from the group consisting of oxygen gas and carbon dioxide gas.

29. The apparatus of claim 19,
further comprising a laser system configured to direct a laser pulse into the sample region.

* * * * *